(12) United States Patent
Sawada et al.

(10) Patent No.: US 9,118,028 B2
(45) Date of Patent: Aug. 25, 2015

(54) ORGANIC ELECTROLUMINESCENT DEVICE

(75) Inventors: Yuichi Sawada, Kitakyushu (JP);
Masanori Hotta, Kitakyushu (JP);
Megumi Matsumoto, Kitakyushu (JP)

(73) Assignee: NIPPON STEEL & SUMIKIN CHEMICAL CO., LTD., Tokyo (JP)

(*) Notice: Subject to any disclaimer, the term of this patent is extended or adjusted under 35 U.S.C. 154(b) by 356 days.

(21) Appl. No.: 13/818,671

(22) PCT Filed: Aug. 22, 2011

(86) PCT No.: PCT/JP2011/068867
§ 371 (c)(1),
(2), (4) Date: Feb. 23, 2013

(87) PCT Pub. No.: WO2012/035934
PCT Pub. Date: Mar. 22, 2012

(65) Prior Publication Data
US 2013/0200350 A1    Aug. 8, 2013

(30) Foreign Application Priority Data

Sep. 13, 2010   (JP) .................................. 2010-204103

(51) Int. Cl.
| | |
|---|---|
| *H01L 51/50* | (2006.01) |
| *C07D 487/04* | (2006.01) |
| *C07D 491/048* | (2006.01) |
| *C07D 495/04* | (2006.01) |
| *H01L 51/00* | (2006.01) |
| *C09K 11/06* | (2006.01) |
| *H05B 33/10* | (2006.01) |

(Continued)

(52) U.S. Cl.
CPC .......... *H01L 51/5012* (2013.01); *C07D 487/04* (2013.01); *C07D 491/048* (2013.01); *C07D 495/04* (2013.01); *C09K 11/06* (2013.01); *H01L 51/0072* (2013.01); *H05B 33/10* (2013.01); *H01L 51/0087* (2013.01); *H01L 51/5016* (2013.01)

(58) Field of Classification Search
None
See application file for complete search history.

(56) References Cited

U.S. PATENT DOCUMENTS 7,541,736 B2 *  6/2009  Sohn et al. .................... 313/504
7,834,198 B2 * 11/2010  Takimiya et al. ............... 549/42

(Continued)

FOREIGN PATENT DOCUMENTS

JP    2009-54809 A      3/2009
JP    2009-246139 A    10/2009

(Continued)

OTHER PUBLICATIONS

International Search Report for the Application No. PCT/JP2011/068867 mailed Oct. 25. 2011.

(Continued)

*Primary Examiner* — Robert S Loewe
(74) *Attorney, Agent, or Firm* — Cheng Law Group, PLLC

(57) ABSTRACT

Provided is an organic electroluminescent device (organic EL device) that is improved in luminous efficiency, sufficiently secures driving stability, and has a simple configuration. The device comprises a plurality of organic layers between an anode and a cathode piled one upon another on a substrate wherein at least one of the organic layers contains a nitrogen-containing organic compound represented by the following formula (1). In formula (1), X is N-A, an oxygen atom, or a sulfur atom; A is an alkyl group, a cycloalkyl group, an aromatic hydrocarbon group, or an aromatic heterocyclic group; and R is a hydrogen atom, an alkyl group, a cycloalkyl group, an aromatic hydrocarbon group, or an aromatic heterocyclic group.

12 Claims, 1 Drawing Sheet

(56) References Cited

U.S. PATENT DOCUMENTS

| | | | |
|---|---|---|---|
| 2003/0228487 A1* | 12/2003 | Lin | 428/690 |
| 2011/0166362 A1 | 7/2011 | Miyata et al. | |
| 2011/0226338 A1* | 9/2011 | Lu et al. | 136/263 |
| 2012/0273764 A1 | 11/2012 | Yu et al. | |

FOREIGN PATENT DOCUMENTS

| | | |
|---|---|---|
| JP | 2009-246140 A | 10/2009 |
| JP | 2010-177644 A | 8/2010 |
| JP | 2010-205815 A | 9/2010 |
| WO | WO-2010/041687 A1 | 4/2010 |
| WO | WO-2011/055933 A2 | 5/2011 |

OTHER PUBLICATIONS

International Preliminary Report on Patentability for Application No. PCT/JP2011/068867 mailed Apr. 18, 2013.

Jin, Youngeup et al., "New Conjugated Polymer Based on Dihydroindoloindole for LEDs", Bull. Korean Chem. Soc., 2006, vol. 27, No. 7, pp. 1043-1047.

Supplementary European Search Report for the Application No. EP 11 82 4942 dated Sep. 30, 2014.

* cited by examiner

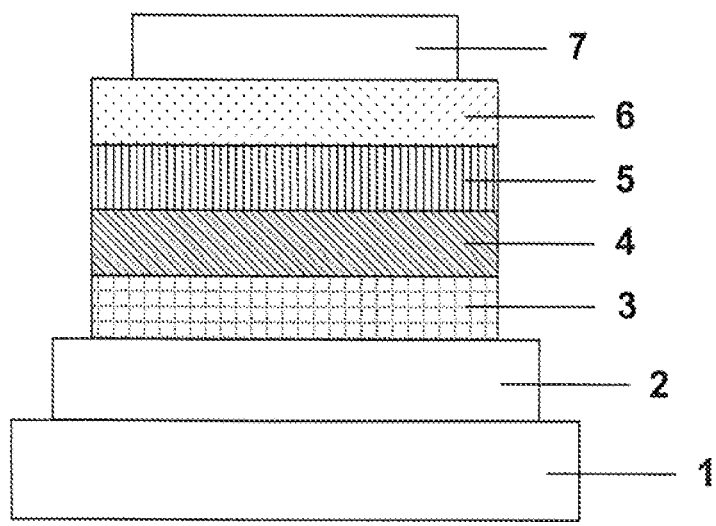

ORGANIC ELECTROLUMINESCENT DEVICE

TECHNICAL FIELD

This invention relates to an organic electroluminescent device containing a nitrogen-containing aromatic compound and, more particularly, to a thin film device that emits light upon application of an electric field to a light-emitting layer composed of an organic compound.

BACKGROUND TECHNOLOGY

An organic electroluminescent device (hereinafter referred to as organic EL device) in the simplest structure is generally constituted of a light-emitting layer and a pair of counter electrodes holding the light-emitting layer between them. The organic EL device functions by utilizing the following phenomenon; upon application of an electric field between the electrodes, electrons are injected from the cathode and holes are injected from the anode and they recombine in the light-emitting layer with emission of light.

In recent, years, studies have been initiated to develop organic EL devices in which organic thin films are used. In particular, in order to enhance the luminous efficiency, the kind of electrodes has been optimized for the purpose of improving the efficiency of injecting carriers from the electrodes and a device has been developed in which a hole-transporting layer composed of an aromatic diamine and a light-emitting layer composed of 8-hydroxyquinoline aluminum complex (Alq3) are disposed in thin film between the electrodes. This device has brought about a marked improvement in the luminous efficiency over the conventional devices utilizing single crystals of anthracene and the like and thereafter the developmental works of organic EL devices have been directed toward practical applications to high-performance flat panels featuring self-luminescence and high-speed response.

Further, in an effort to enhance the luminous efficiency of the device, the use of phosphorescence in place of fluorescence is investigated. The aforementioned device comprising a hole-transporting layer composed of an aromatic diamine and a light-emitting layer composed of Alq3 and many others have utilized fluorescence. The use of phosphorescence, that is, emission of light from the triplet excited state, is expected to enhance the luminous efficiency three to four times that of the conventional devices using fluorescence (emission of light from the singlet excited state). To achieve this objective, the use of coumarin derivatives and benzophenone derivatives in the light-emitting layer was investigated, but these derivatives merely produced luminance at an extremely low level. Europium complexes were also investigated in trials to utilize the excited triplet state, but they failed to emit light at high efficiency. In recent years, as described in patent document 1, a large number of researches are conducted on phosphorescent dopant materials, with a focus on the use of organic metal complexes such as iridium complexes, for the purpose of enhancing the luminous efficiency and extending the life.

PRIOR ART TECHNICAL DOCUMENTS

Patent Documents

Patent document 1: JP 2003-515897 A
Patent document 2: JP 2001-313178 A
Patent document 3: JP 2009-054809 A
Patent document 4: JP 2009-246139 A
Patent document 5: JP 2009-246140 A In order to obtain high luminous efficiency, a host material to be used together with the aforementioned dopant material becomes important. Of the host materials proposed thus far, a typical example is 4,4'-bis(9-carbazolyl)biphenyl (hereinafter referred to as CBP), a carbazole compound presented in patent document 2. Since CBP is characterized by having a good hole transfer property but a poor electron transfer property, the use of CBP as a host material for tris(2-phenylpyridine)iridium complex (hereinafter referred to as Ir(ppy)3), a typical phosphorescent green light-emitting material, disturbs the balanced injection of charges and causes an excess of holes to flow out to the side of the electron-transporting layer. The results is a reduction in the luminous efficiency of Ir(ppy)3.

In order for organic EL devices to display high luminous efficiency, host materials that have high triplet excitation energy and are well balanced in the injection and transport characteristics of electric charges (holes and electrons) are required. Furthermore, compounds that are electrochemically stable, highly resistant to heat, and excellently stable in the amorphous state are desired and further improvements are demanded.

Patent document 3 discloses the indoloindole compound illustrated below. However, this compound is intended for limited use as an organic transistor material and the document does not disclose the effectiveness of this compound as an organic EL material, particularly as a phosphorescent host material.

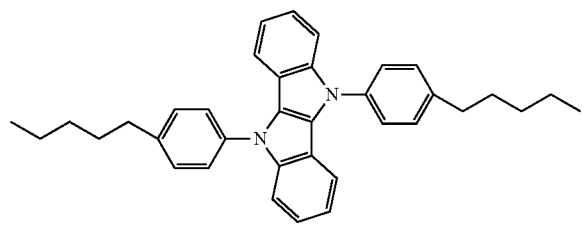 [SMILES: CCCCCc1ccc(-n2c3ccccc3c3c2c2ccccc2n3-c2ccc(CCCCC)cc2)cc1]

Patent documents 4 and 5 disclose organic EL devices using the compounds illustrated below.

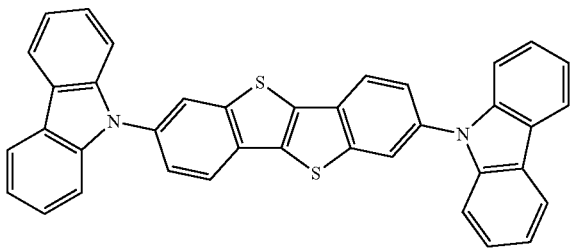

-continued

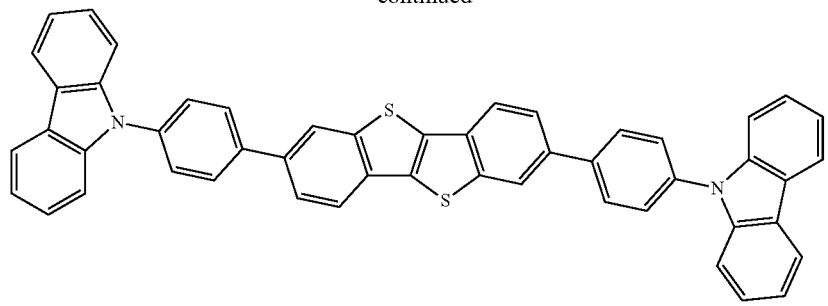

However, these documents disclose only organic EL devices using compounds that have a benzochalcogeno[3,2-b]benzochalcogenophene skeleton and do not disclose the effectiveness of nitrogen-containing aromatic compounds having a structure formed by fusing an indole ring to a fused heterocycle.

DISCLOSURE OF THE INVENTION

In applications of organic EL devices to display devices such as flat panel displays, it is necessary to enhance the luminous efficiency of the device and, at the same time, to sufficiently secure the driving stability of the device. Under the aforementioned circumstances, an object of this invention is to provide an organic EL device exhibiting such luminous efficiency and driving stability as to be practically useful and to provide a compound suitable therefor.

The inventors of this invention have conducted intensive studies, found that an organic EL device using a nitrogen-containing aromatic compound that is formed by fusing indole to a fused heterocycle consisting of a five-membered ring and a six-membered ring displays excellent characteristics, and completed this invention.

This invention relates to an organic electroluminescent, device comprising an anode, a plurality of organic layers, and a cathode piled one upon another on a substrate wherein at least one of the organic layers contains a nitrogen-containing aromatic compound represented by general formula (1).

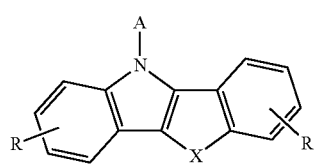

(1)

In general formula (1), X is N-A, an oxygen atom, or a sulfur atom; each A is independently an alkyl group of 1 to 10 carbon atoms, a cycloalkyl group of 3 to 11 carbon atoms, an aromatic hydrocarbon group of 6 to 30 carbon atoms, or an aromatic heterocyclic group of 3 to 30 carbon atoms exclusive of a fused heterocycle consisting of 4 rings or more; each R is independently a hydrogen atom, an alkyl group of 1 to 10 carbon atoms, a cycloalkyl group of 3 to 11 carbon atoms, an aromatic hydrocarbon group of 6 to 18 carbon atoms, or an aromatic heterocyclic group of 3 to 18 carbon atoms exclusive of a fused heterocycle consisting of 4 rings or more.

Of the nitrogen-containing aromatic compounds represented by general formula (1), those in which each A is independently an aromatic hydrocarbon group of 6 to 30 carbon atoms or an aromatic heterocyclic group of 3 to 30 carbon atoms exclusive of a fused heterocycle consisting of 4 rings or more are preferred. Further, those in which X is NA are preferred.

It is preferable that the organic layer containing a nitrogen-containing aromatic compound represented by general formula (1) is at least one layer selected from the group consisting of a light-emitting layer, a hole-transporting layer, and an electron-blocking layer. It is more preferable that the layer in question is a light-emitting layer containing a phosphorescent dopant.

BRIEF DESCRIPTION OF THE DRAWING

FIG. 1 is a cross section illustrating an example of the structure of an organic EL device.

PREFERRED EMBODIMENTS OF THE INVENTION

The organic electroluminescent device of this invention contains a nitrogen-containing aromatic compound represented by the aforementioned general formula (1) (hereinafter referred to as a compound represented by general formula (1) or a nitrogen-containing aromatic compound). This nitrogen-containing aromatic compound assumes a configuration formed by [3,2-b]-fusion of a fused heterocycle to a five-membered indole ring and this particular configuration seems to produce the aforementioned excellent effect.

In general formula (1), X is N-A, an oxygen atom, or a sulfur atom. Preferably, X is N-A.

In general formula (1), A is an alkyl group of 1 to 10 carbon atoms, a cycloalkyl group of 3 to 11 carbon atoms, an aromatic hydrocarbon group of 6 to 30 carbon atoms, or an aromatic heterocyclic group of 3 to 30 carbon atoms exclusive of a fused heterocycle consisting of 4 rings or more; preferably, A is an alkyl group of 1 to 8 carbon atoms, a cycloalkyl group of 3 to 7 carbon atoms, an aromatic hydrocarbon group of 6 to 24 carbon atoms, or an aromatic heterocyclic group of 3 to 24 carbon atoms exclusive of a fused heterocycle consisting of 4 rings or more more preferably, A is an aromatic hydrocarbon group of 6 to 24 carbon atoms or an aromatic heterocyclic group of 3 to 24 carbon atoms exclusive of a fused heterocycle consisting of 4 rings or more. In the case where X is N-A, two As in general formula (1) may be identical with or different from each other.

Specific examples of the alkyl group include a methyl group, an ethyl group, propyl group, a butyl group, a pentyl group, a hexyl group, a heptyl group, an octyl group, a nonyl group, and a decyl group. Preferable examples include a methyl group, an ethyl group, a propyl group, a butyl group, a pentyl group, a hexyl group, a heptyl group, and an octyl group. Any of the aforementioned alkyl groups may be linear or branched.

Specific examples of the cycloalkyl group include a cyclopropyl group, a cyclobutyl group, a cyclopentyl group, a cyclohexyl group, a cycloheptyl group, a cyclooctyl group, and a methy cyclohexyl group; a cyclohexyl group and a methylcyclohexyl group are preferred.

Specific examples of the aromatic hydrocarbon group and the aromatic heterocyclic group exclusive of a fused heterocycle consisting of 4 rings or more include monovalent groups formed by removing a hydrogen atom from benzene, pentalene, indene, naphthalene, azulene, heptalene, octalene, indacene, acenaphthylene, phenalene, phenanthrene, anthracene, trindene, fluoranthene, acephenanthrylene, aceanthrylene, triphenylene, pyrene, chrysene, tetraphene, pleiadene, picene, perylene, pentaphene, pentacene, tetraphenylene, cholanthrylene, helicene, hexaphene, rubicene, coronene, trinaphthylene, heptaphene, pyranthrene, furan, benzofuran, isobenzofuran, xanthene, oxanthrene, dibenzofuran, perixanthenoxanthene, thiophene, thioxanthene, thianthrene, phenoxathiine, thionaphthene, isothianaphthene, thiophthene, thiophanthrene, dibenzothiophene, pyrrole, pyrazole, tellurazole, selenazole, thiazole, isothiazole, oxazole, furazan, pyridine, pyrazine, pyrimidine, pyridazine, triazine, indolizine, indole, isoindole, indazole, purine, quinolizine, isoquinoline, carbazole, imidazole, naphthyridine, phthalazine, quinazoline, benzodiazepine, quinoxaline, cinnoline, quinoline, pteridine, phenanthridine, acridine, perimidine, phenanthroline, phenazine, carboline, phenotellurazine, phenoselenazine, phenothiazine, phenoxazine, anthyridine, benzothiazole, benzimidazole, benzoxazole, benzisoxazole, and benzoisothiazole or from aromatic compounds in which a plurality of these aromatic rings are linked together. Preferable examples include monovalent groups formed by removing a hydrogen atom from benzene, naphthalene, anthracene, pyridine, pyrazine, pyrimidine, pyridazine, triazine, isoindole, indazole, purine, isoquinoline, imidazole, naphthyridine, phthalazine, quinazoline, benzodiazepine, quinoxaline, cinnoline, quinoline, pteridine, phenanthridine, acridine, perimidine, phenanthroline, phenazine, carboline, indole, and carbazole or from aromatic compounds in which a plurality of these aromatic rings are linked together.

In the case of the groups that are derived from aromatic compounds in which a plurality of aromatic rings are linked together, the number of the aromatic rings to be linked is preferably 2 to 10, more preferably 2 to 7, and the aromatic rings to be linked may be identical with or different from one another. In such a case, the position at which A is linked to the nitrogen atom in the ring represented by formula (1) is not limited and it may be a ring at the end or in the middle of the linked aromatic rings. Here, the aromatic ring is used as a general term to mean both an aromatic hydrocarbon ring and an aromatic heterocycle. In the case where a group consisting of linked aromatic rings contains at least one heterocycle, the group is included in aromatic heterocyclic groups.

The monovalent groups derived from compounds in which a plurality of aromatic rings are linked together are represented, for example, by the following formulas.

(11)

(12)

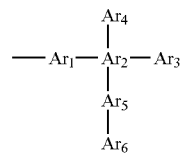

(13)

(In formulas (11) to (13), each of $Ar_1$ to $Ar_6$ is a substituted or unsubstituted aromatic ring.)

Specific examples of the aforementioned groups formed from compounds in which a plurality of aromatic rings are linked too-ether include monovalent groups formed by removing a hydrogen atom from biphenyl, terphenyl, bipyridine, bipyrimidine, bitriazine, terpyridine, bistriazylbenzene, dicarbazolylbenzene, carbazolylbiphenyl, dicarbazolylbiphenyl, phenylterphenyl, carbazolylterphenyl, binaphthalene, phenylpyridine, phenylcarbazole, diphenylcarbazole, biphenylpyridine, phenylpyrimidine, diphenylpyrimidine, phenyltriazine, diphenyltriazine, phenylnaphtbalene, and diphenylnaphthalene.

An aromatic heterocyclic group exclusive of a fused heterocycle consisting of 4 rings or more means an aromatic heterocyclic group consisting of a single ring or a fused aromatic heterocyclic group consisting of 2 or 3 rings and the group may have a substituent. In the case where this aromatic heterocyclic group consists of a plurality of aromatic rings linked together in the manner represented, for example, by formula (11), each of these aromatic rings can never be a fused heterocycle consisting of 4 rings or more.

The aforementioned aromatic hydrocarbon group or aromatic heterocyclic group exclusive of a fused heterocycle consisting of 4 rings or more may have a substituent. When a substituent is present, examples of such a substituent include an alkyl group of 1 to 4 carbon atoms, a cycloalkyl group of 3 to 6 carbon atoms, an alkoxyl group of 1 to 2 carbon atoms, an acetyl group, an amino group of 6 to 18 carbon atoms, a phosphanyl group of 6 to 18 carbon atoms, and a silyl group of 3 to 18 carbon atoms. Preferable examples include an alkyl group of 1 to 4 carbon atoms, a cycloalkyl group of 3 to 6 carbon atoms, and an amino group of 6 to 15 carbon atoms. In this case, an aromatic group linked as a branch is not treated as a substituent.

In the case where A is an aromatic hydrocarbon group, an aromatic heterocyclic group, or an aliphatic hydrocarbon group and has a substituent, the number of substituents is 1 to 10, preferably 1 to 6, more preferably 1 to 4. In the case where two or more substituents are present, they may be identical with or different from one another. In computing the number of carbon atoms in the aforementioned aromatic hydrocarbon group, aromatic heterocyclic group, or aliphatic hydrocarbon group, the total number of carbon atoms includes that of carbon atoms in a substituent if any.

In general formula (1), A is preferably an aromatic hydrocarbon group or an aromatic heterocyclic group. Specific examples of the aromatic hydrocarbon group and the aromatic heterocyclic group include monovalent groups formed by removing a hydrogen atom from benzene, naphthalene, anthracene, pyridine, pyrimidine, triazine, carbazole, dibenzofuran, dibenzothiophene, biphenyl, terphenyl, dicarbazolylbenzene, carbazolylbiphenyl, dicarbazolylbiphenyl, phenylterphenyl, phenylpyridine, phenylcarbazole, diphenylcarbazole, diphenylpyridine, diphenylpyrimidine, and diphenyltriazine.

In general formula (1), each R is independently a hydrogen atom, an alkyl group of 1 to 10 carbon atoms, a cycloalkyl group of 3 to 11 carbon atoms, an aromatic hydrocarbon group of 6 to 18 carbon atoms, or an aromatic heterocyclic group of 3 to 18 carbon atoms exclusive of a fused heterocycle consisting of 4 rings or more preferably a hydrogen atom, an alkyl group of 1 to 4 carbon atoms, a cycloalkyl group of 3 to 6 carbon atoms, an aromatic hydrocarbon group of 6 to 12 carbon atoms, or an aromatic heterocyclic group of 3 to 12 carbon atoms exclusive of a fused heterocycle consisting of 4 rings or more; more preferably a hydrogen atom, a phenyl group, or a carbazolyl group.

A compound represented by general formula (I) can be synthesized by a known method by using a 2-bromonitrobenzene derivative as a starting material and selecting raw materials according to the structure of the target compound.

For example, an indoloindole compound or a compound represented by general formula (1) wherein X is N-A can be synthesized by the reactions shown below by formula with reference to synthetic examples described in J. Org. Chem., 2009, 4242-4246, Journal of Medicinal Chemistry, 2003, 2436-2445, and J. Am. Chem. Soc., 1994, 8152-8161.

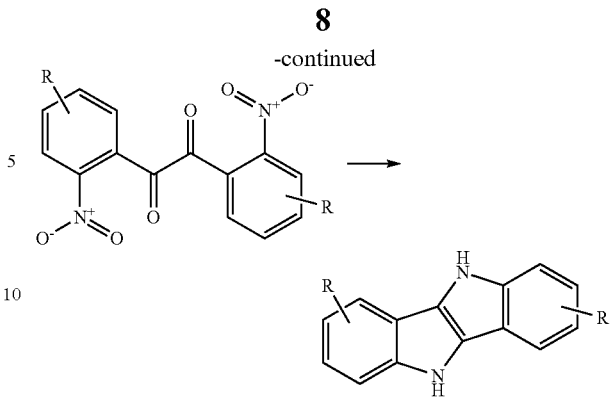

A benzofuroindole compound or a compound represented by general formula (1) wherein X is an oxygen atom can be synthesized by the reactions shown below by formula with reference to synthetic examples described in Heterocycles, 1990, Vol. 31, 1951-1958 and Journal of Chemical Research, 1988. 272-273.

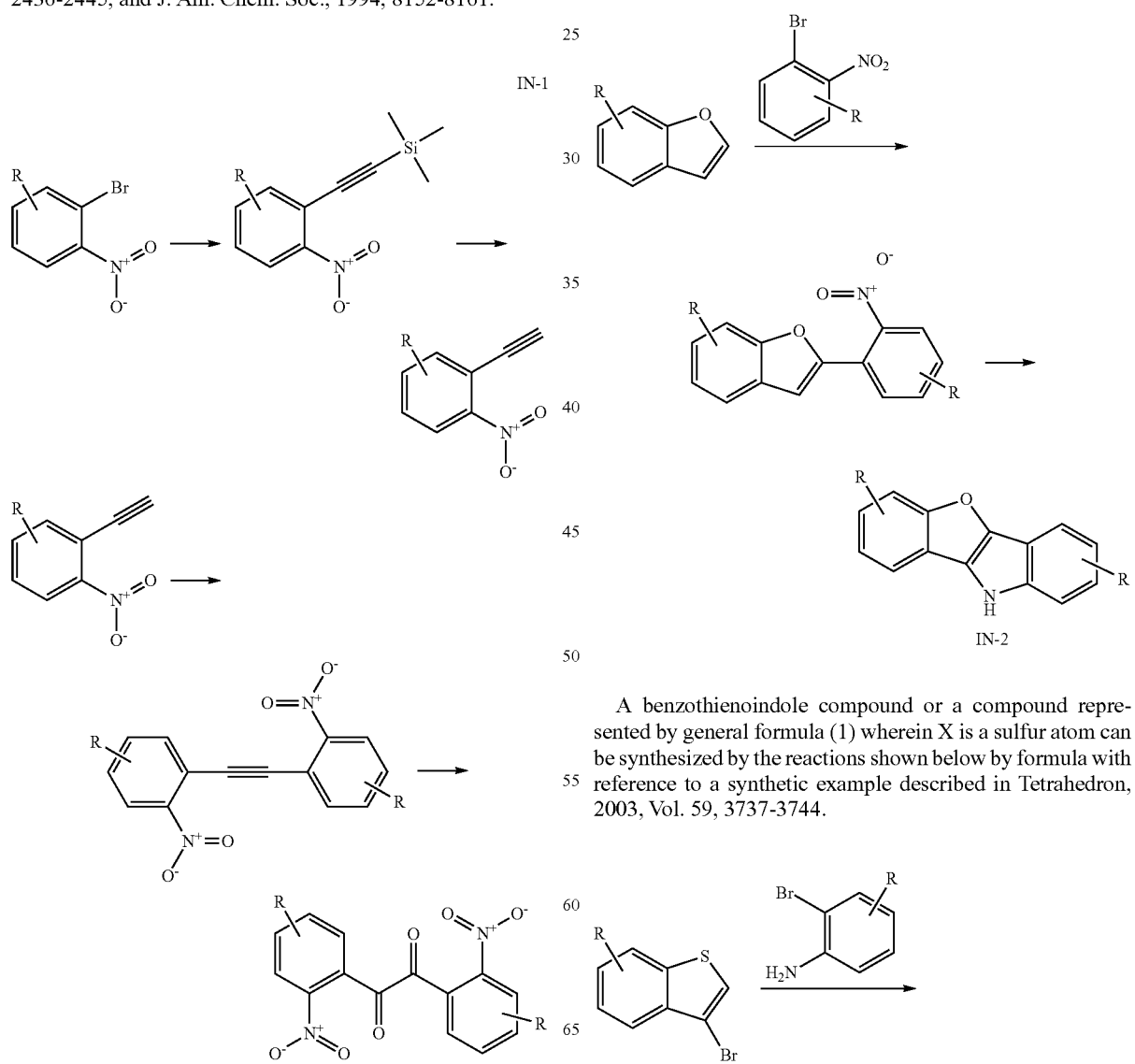

A benzothienoindole compound or a compound represented by general formula (1) wherein X is a sulfur atom can be synthesized by the reactions shown below by formula with reference to a synthetic example described in Tetrahedron, 2003, Vol. 59, 3737-3744.

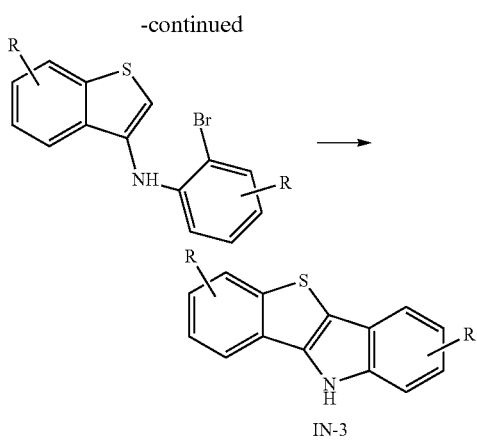

IN-3

The aforementioned reactions yield products, of an indoloindole skeleton formed by fusion of indole to a heterocycle consisting of 2 rings. The hydrogen atom linked to the nitrogen atom in each of these compounds can be substituted with a suitable group by a coupling reaction such as the Ullmann reaction to yield a compound represented by general formula (1).

Specific examples of the nitrogen-containing aromatic compounds represented by general formula (1) are illustrated below, but materials suitable for use in the organic electroluminescent, devices of this invention are not limited to these compounds.

(1-1)

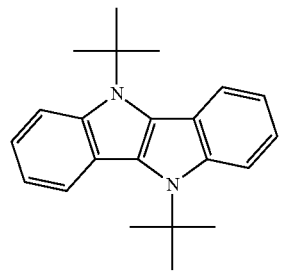

(1-2)

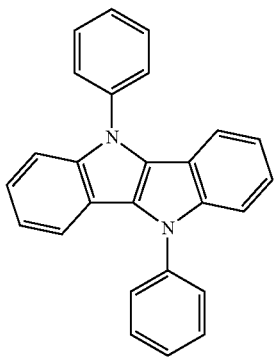

(1-3)

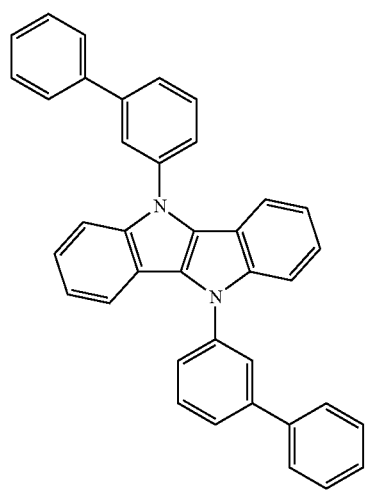

(1-4)

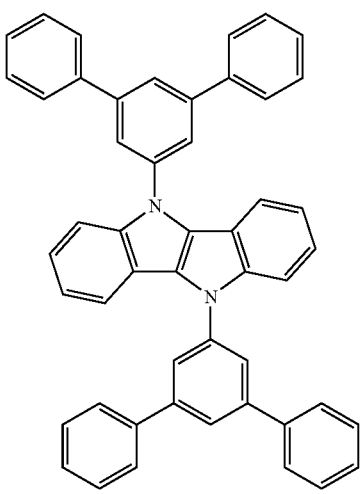

-continued
(1-5)
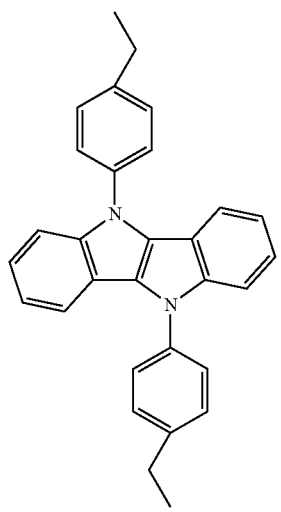
(1-6)
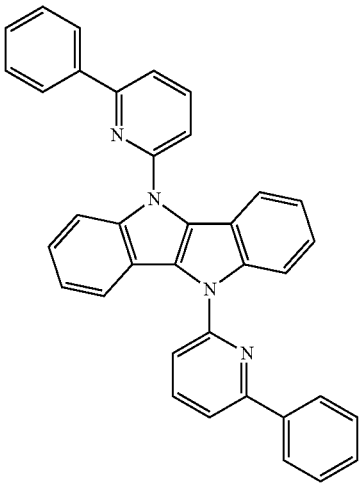
(1-7)
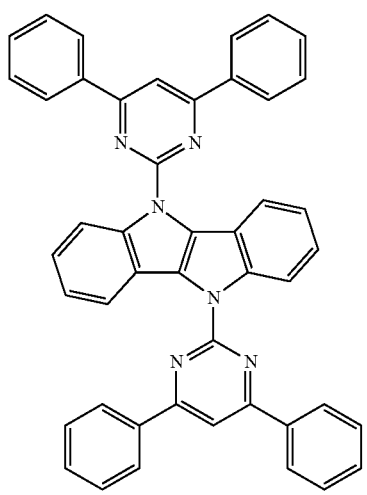
(1-8)
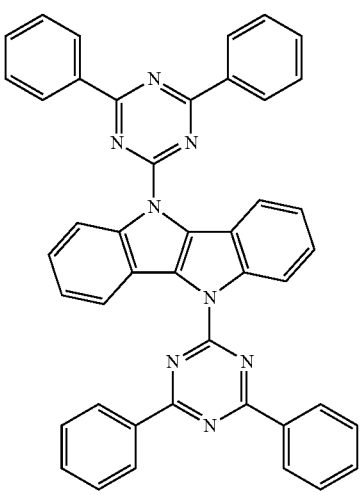

-continued
(1-9)
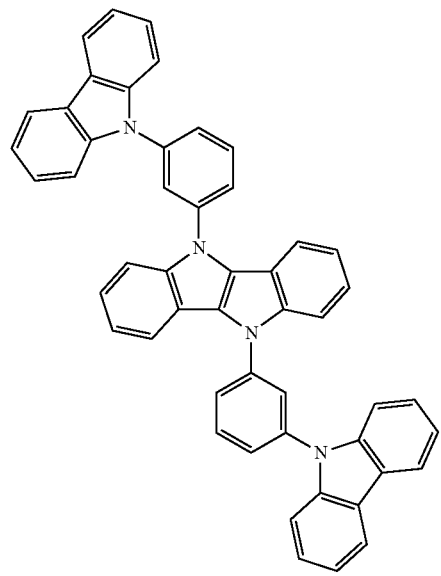
(1-10)
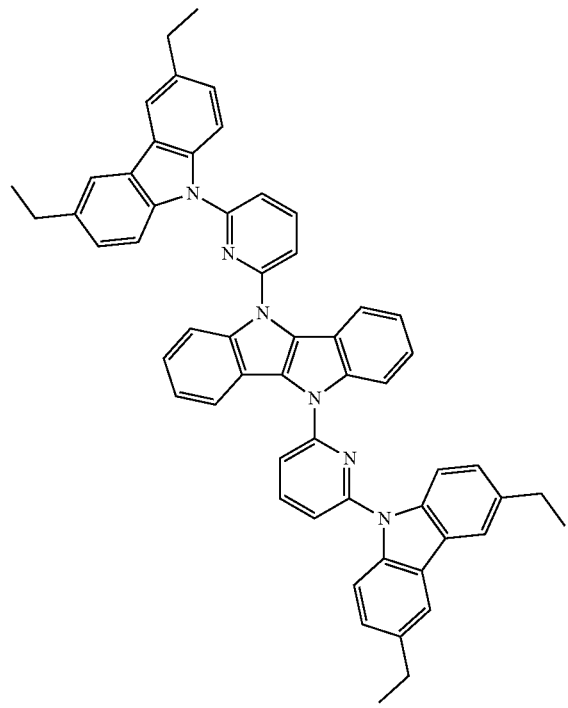
(1-11)
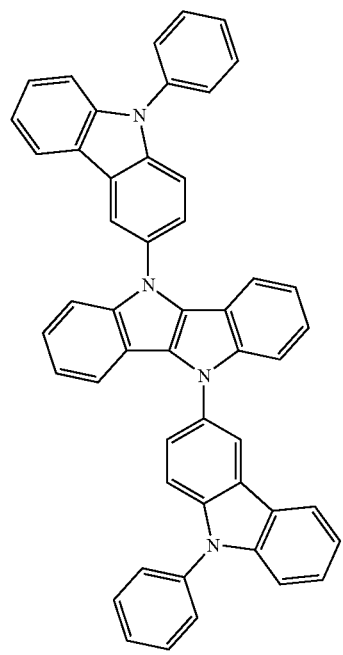
(1-12)
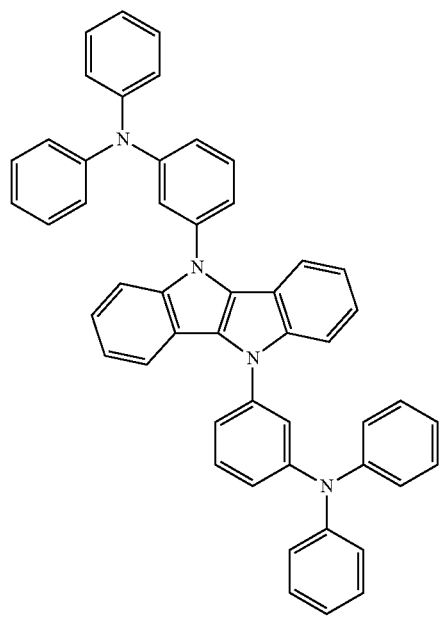

-continued
(1-13)
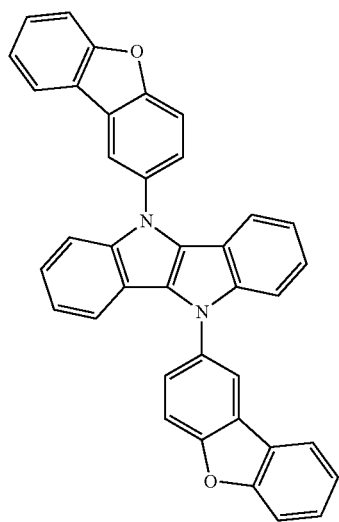
(1-14)
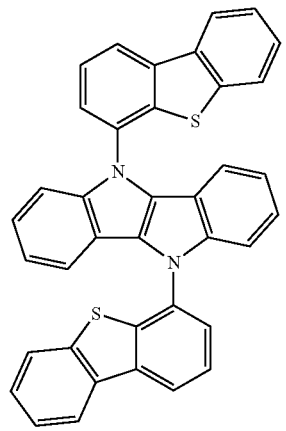
(1-15)
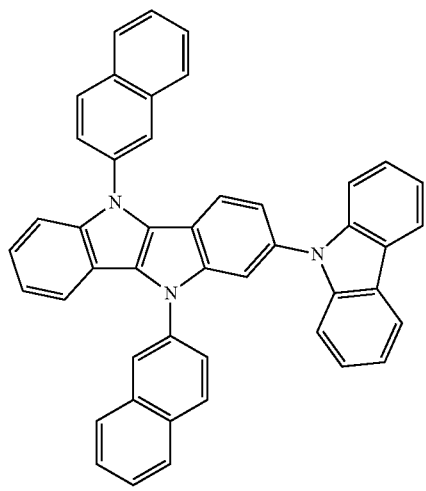
(1-16)
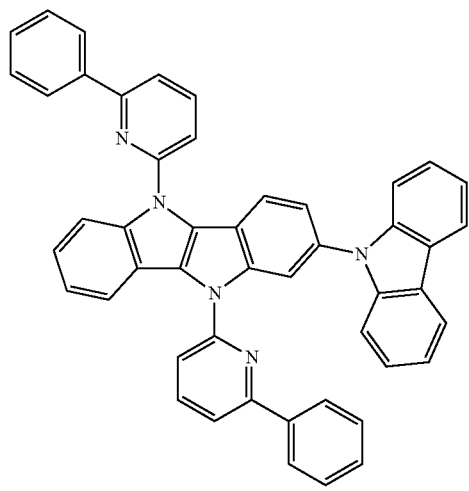
(1-17)
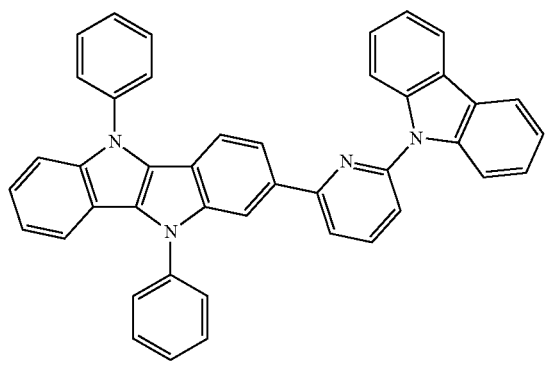
(1-18)
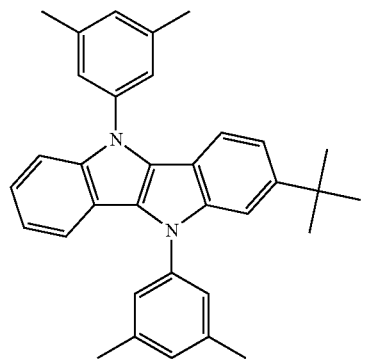

-continued
(1-19)
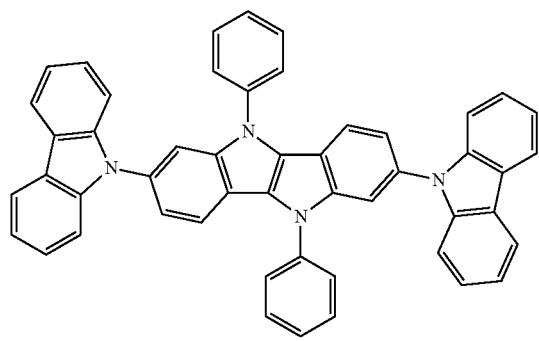
(1-20)
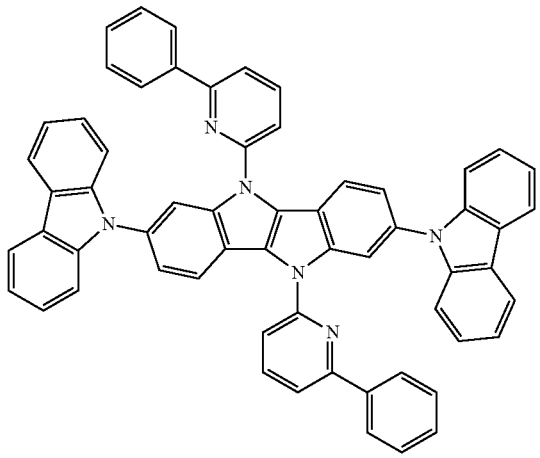
(1-21)
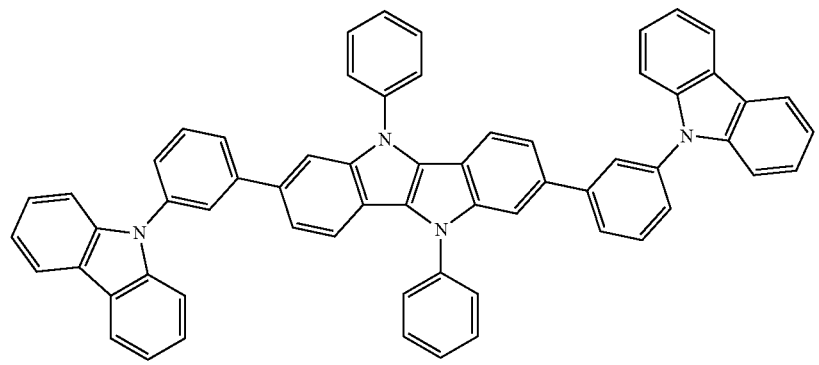
(1-22)
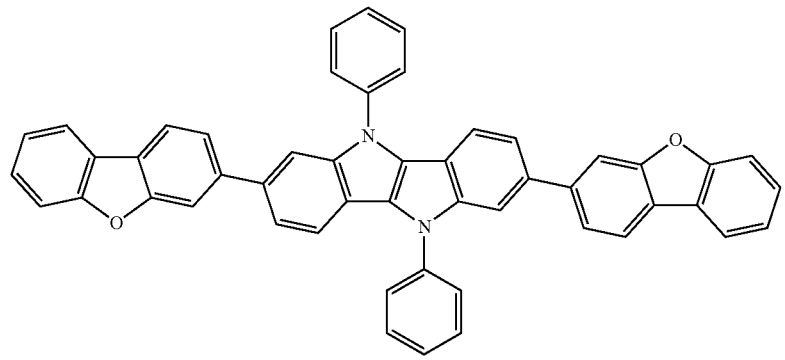
(1-23)
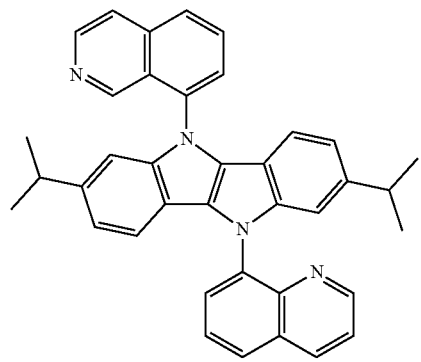
(2-1)
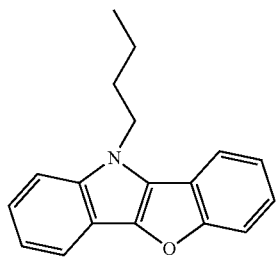

-continued
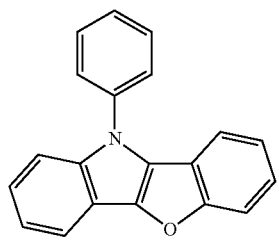
(2-2)
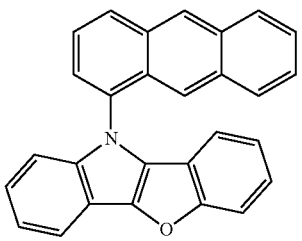
(2-3)
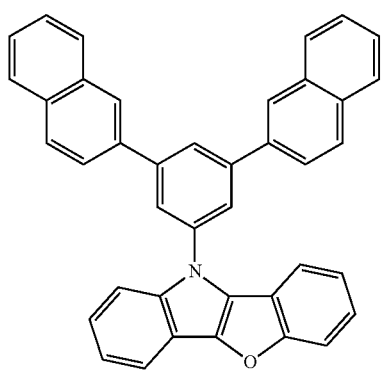
(2-4)
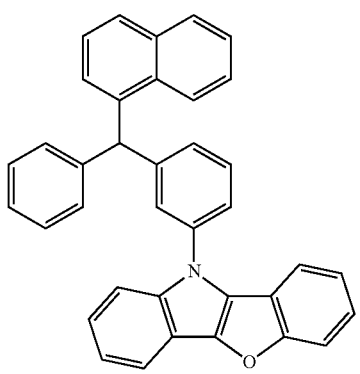
(2-5)
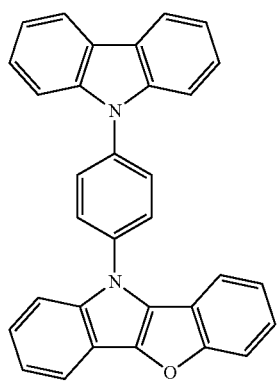
(2-6)
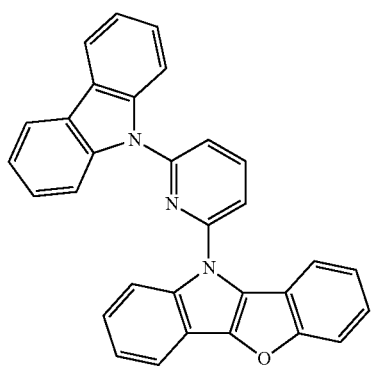
(2-7)
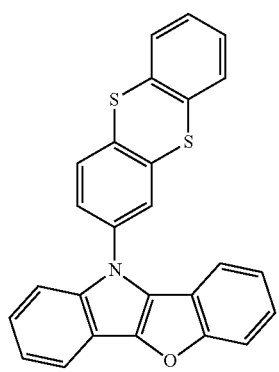
(2-8)
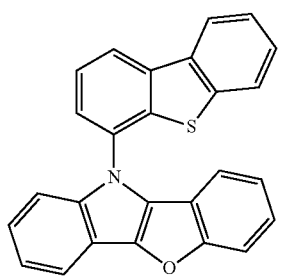
(2-9)

-continued
(2-10)
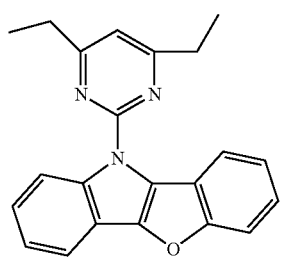
(2-11)
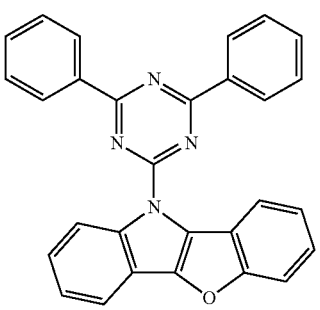
(2-12)
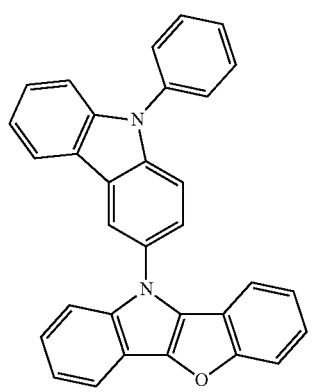
(2-13)
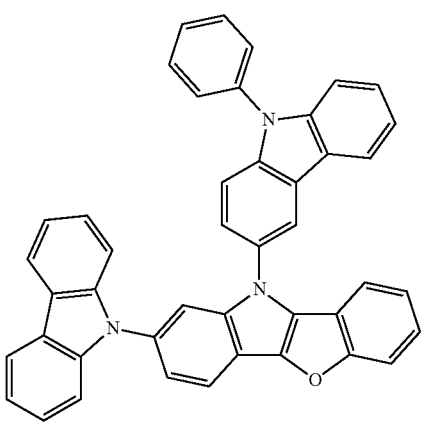
(2-14)
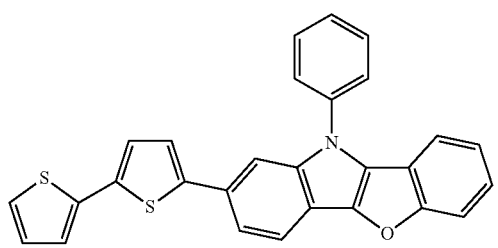
(2-15)
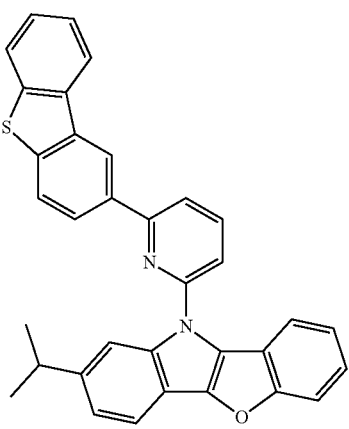
(2-16)
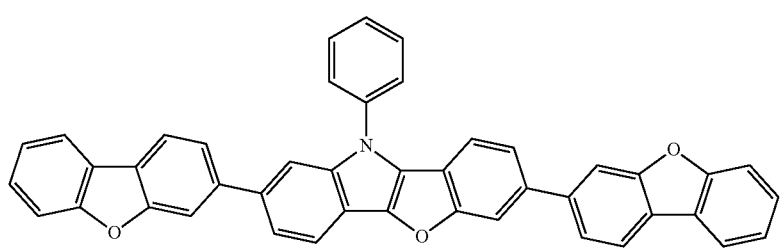

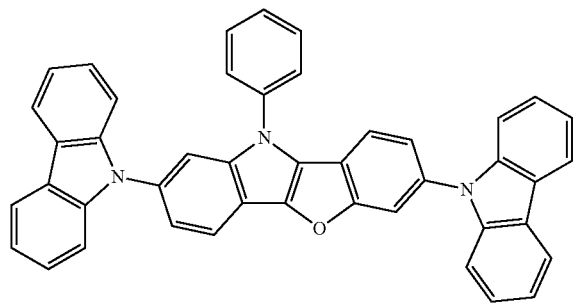
(2-17)
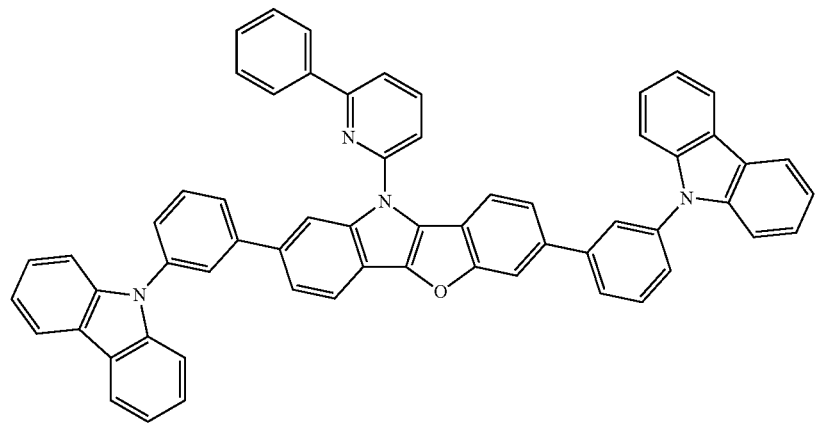
(2-18)
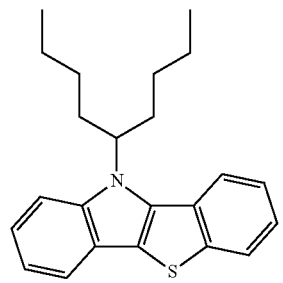
(3-1)
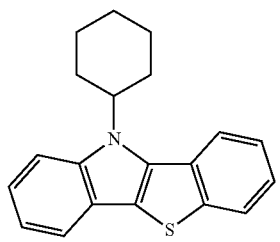
(3-2)
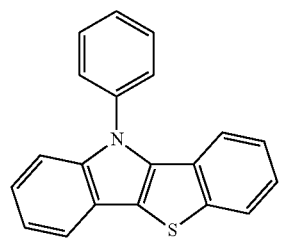
(3-3)
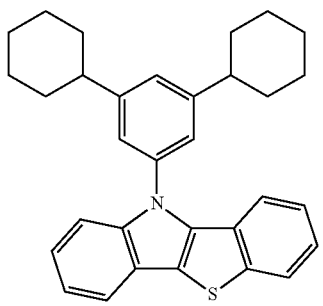
(3-4)

-continued
(3-5)
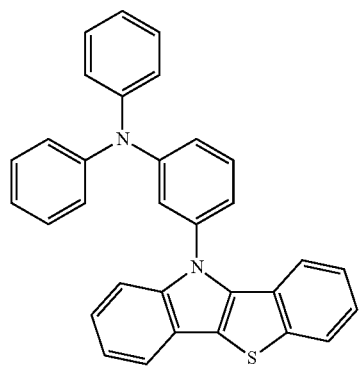
(3-6)
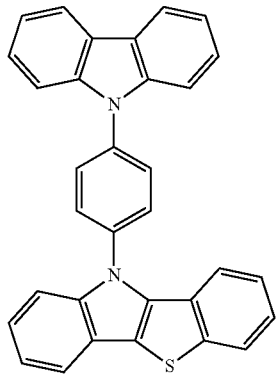
(3-7)
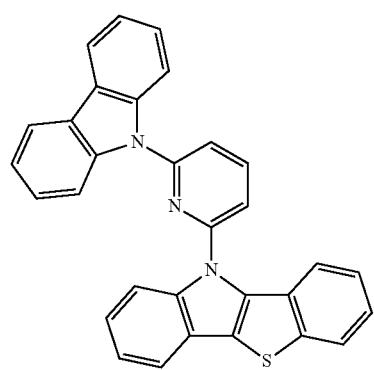
(3-8)
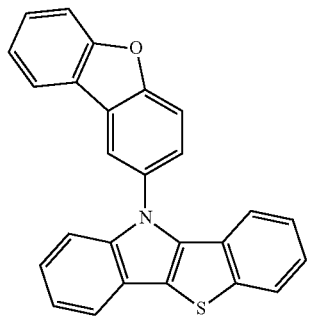
(3-9)
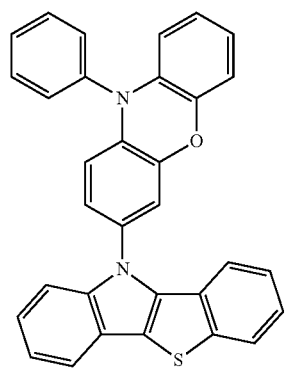
(3-10)
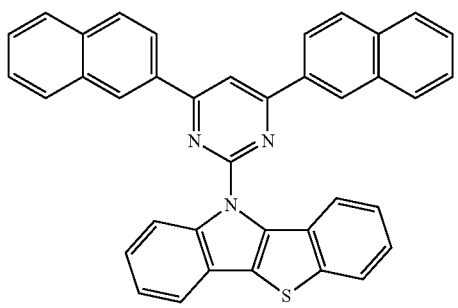
(3-11)
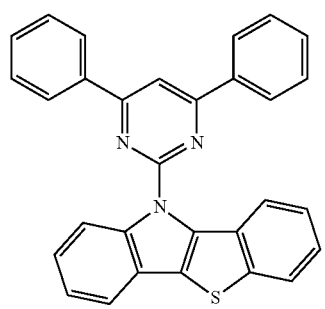
(3-12)
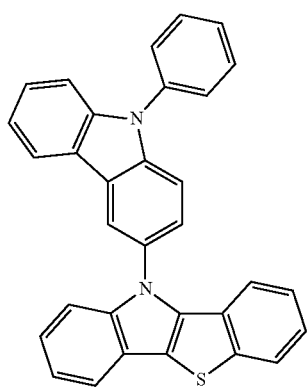

-continued
(3-13)
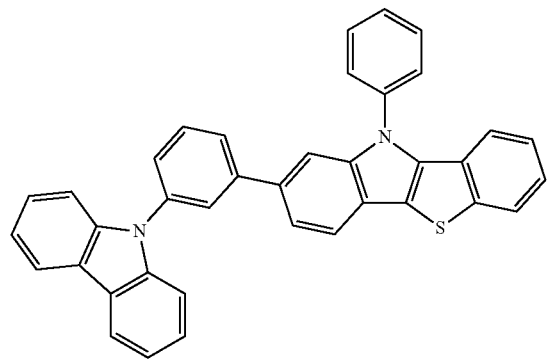
(3-14)
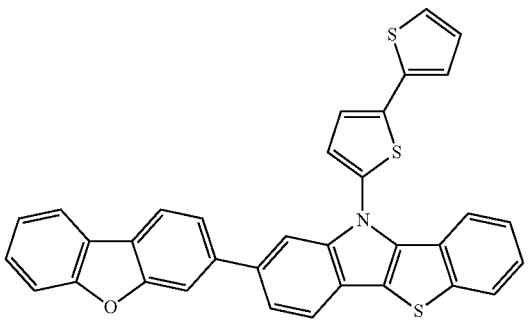
(3-15)
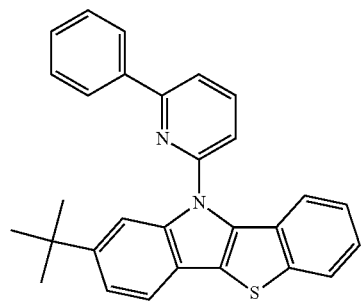
(3-16)
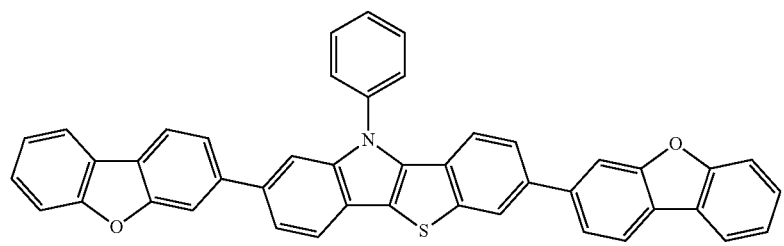
(3-17)
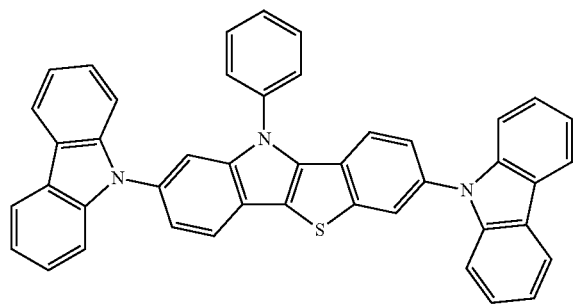

-continued (3-18)

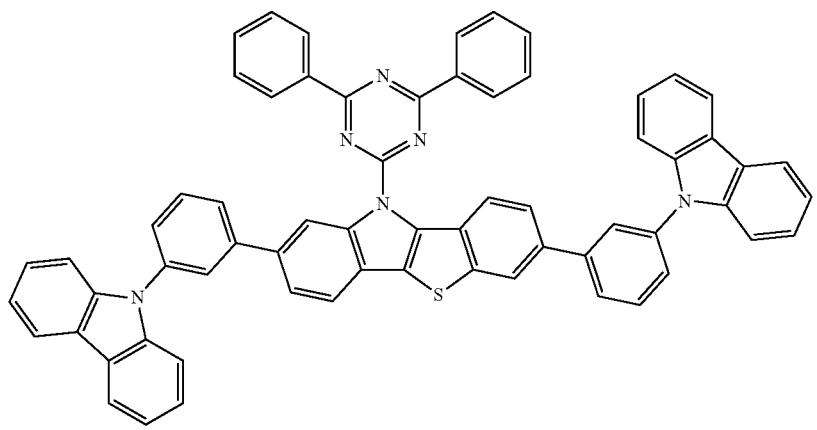

Provided that an organic EL device comprises an anode, a plurality of organic layers, and a cathode piled one upon another on a substrate, incorporation of a nitrogen-containing aromatic compound represented by general formula (1) in at least one of the organic layers helps provide an excellent organic EL device. An organic layer suitable for this purpose is a light-emitting layer, a hole-transporting layer, or an electron-blocking layer. Preferably; the nitrogen-containing aromatic compound is incorporated as a host material in a light-emitting layer containing a phosphorescent dopant.

An organic EL device according to this invention is explained hereinafter.

The organic EL device of this invention comprises organic layers at least one of which is a light-emitting layer between an anode and a cathode piled one upon another on a substrate and, further, at least one organic layer contains a compound represented by general formula (1). Advantageously, a compound represented by general formula (1) is contained in a light-emitting layer, a hole-transporting layer, and an electron-blocking layer. More advantageously, a compound represented by general formula (1) is contained in alight-emitting layer together with a phosphorescent dopant.

The structure of an organic EL device according to this invention is explained hereinafter with reference to the drawing, but it will not be limited to the one illustrated in the drawing.

FIG. 1 is a cross section to illustrate an example of the structure of an organic EL device generally used in this invention and the numbers in FIG. 1 stand for the following: 1 for a substrate, 2 for an anode, 3 for a hole-injecting layer, 4 for a hole-transporting layer, 5 for a light-emitting layer, 6 for an electron-transporting layer, and 7 for a cathode. The organic EL device of this invention may further comprise an exciton-blocking layer adjacent to the light-emitting layer or an electron-blocking layer between the light-emitting layer and the hole-injecting layer. The exciton-blocking layer may be inserted either on the anode side or on the cathode side of the light-emitting layer or may be inserted simultaneously on both sides. The organic EL device of this invention comprises the substrate, the anode, the light-emitting layer, and the cathode as essential layers. However, it is preferable that the device comprises a hole-injecting/transporting layer and an electron-injecting/transporting layer in addition to the essential layers and further comprises a hole-blocking layer between the light-emitting layer and the electron-injecting/transporting layer. The hole-injecting/transporting layer means a hole-injecting layer and/or a hole-transporting layer while the electron-injecting/transporting layer means an electron-injecting layer and/or an electron-transporting layer.

The organic EL device of this invention can be so constructed as to have a structure that is the reverse of the structure illustrated in FIG. 1 by piling the cathode 7, the electron-transporting layer 6, the light-emitting layer 5, the hole-transporting layer 4, and the anode 2 one upon another in this order on the substrate 1. In this case, it is possible to add or omit a layer or layers according to the need.

—Substrate—

The organic EL device of this invention is preferably supported by a substrate. There is no specific restriction on the substrate and any of the substrates that have been used customarily in organic EL devices can be used. A substrate made from a material such as glass, transparent plastic, and quartz may be used.

—Anode—

The anode of an organic EL device is preferably made from an electrode substance having a high work function (4 eV or more) such as a metal, an alloy, an electrically conductive compound, and a mixture thereof. Specific examples of the electrode substances of this kind include metals such as Au and electrically conductive transparent materials such as CuI, indium tin oxide (ITO), $SnO_2$, and ZnO. Further, a material such as IDIXO ($In_2O_3$—ZnO) that is amorphous and formable into a transparent electrically conductive film may be used. The anode may be formed by preparing a thin film from any of those electrode substances by a method such as vapor deposition and sputtering and then forming a pattern of desired shape on the thin film by photolithography. Or, in the case where high accuracy is not required in patterning (100 μm or more), a pattern may be formed through a mask of desired shape during vapor deposition or sputtering of the aforementioned electrode substance. In the case where a substance that is applicable by a coating method such as an electrically conductive organic compound is used, a wet film-forming process such as printing and coating may be employed. When emitted light is taken out from the anode, the transmittance is desirably set at 10% or more and the sheet resistance as the anode is preferably several hundred Ω/□ or less. Further, the thickness of the film is normally selected from the range of 10 to 1,000 nm, preferably 10 to 200 nm, although it varies with the film-forming material.

—Cathode—

Meanwhile, the cathode is made from an electrode substance having a low work function (4 eV or less) such as a metal (hereinafter referred to as electron-injecting metal), an alloy, an electrically conductive compound, and a mixture thereof. Specific examples of the electrode substances of this kind include sodium, a sodium-potassium alloy, magnesium, lithium, a magnesium/copper mixture, a magnesium/silver mixture, a magnesium/aluminum mixture, a magnesium/indium mixture, an aluminum/aluminum oxide ($Al_2O_3$) mixture, indium, a lithium/aluminum mixture, and a rare earth metal. From the viewpoint of electron-injecting property and durability against oxidation and the like, a mixture of an electron-injecting metal and a second metal that is higher in work function and more stable than the electron-injecting metal is suitable for use as, an electrode substance and examples thereof include a magnesium/silver mixture, a magnesium/aluminum mixture, a magnesium/indium mixture, an aluminum/aluminum oxide ($Al_2O_3$) mixture, a lithium/aluminum mixture, and aluminum. The cathode is formed by preparing a thin film from any of those electrode substances by a method such as vapor deposition and sputtering. The sheet resistance as the cathode is preferably several hundred Ω/□ or less and the thickness of the film is selected from the range of 10 nm to 5 µm, preferably in the range of 50 to 200 nm. Making either the anode or the cathode of an organic EL device transparent or translucent in order to transmit emitted light advantageously improves the luminance.

A transparent or translucent cathode may be made by forming a cathode with a film thickness of 1 to 20 nm from the aforementioned metal and then forming thereon a film of one of the electrically conductive transparent materials described above in explanation of the anode. This method can be applied to fabrication of a device in which both the anode and the cathode display good transmittance properties.

—Light-Emitting Layer—

In the case where the light-emitting layer is a fluorescent light-emitting layer, it is allowable to use at least one kind of fluorescent light-emitting material alone as a material in the layer, but it is preferable to use the fluorescent material as a fluorescent dopant and incorporate a host material in the layer.

A compound represented by general formula (1) may be used as a fluorescent light-emitting material in the light-emitting layer. However, other compounds that have been known as fluorescent light-emitting materials in a large number of patent documents and elsewhere may also be used. Examples of such other compounds include benzoxazole derivatives, benzimidazole derivatives, benzothiazole derivatives, styrylbenzene derivatives, polyphenyl derivatives, diphenylbutadiene derivatives, tetraphenylbutadiene derivatives, naphthalimide, derivatives, coumarin derivatives, fused aromatic compounds, perinone derivatives, oxadiazole derivatives, oxazine derivatives, aldazine derivatives, pyrrolizine derivatives, cyclopenta diene derivatives, bisstyrylanthracene derivatives, quinacridone derivatives, pyrrolopyridine derivative, thiadiazolopyridine derivatives, styrylamine derivatives, diketopyrrolopyrrole derivatives, aromatic dimethylidene compounds, a variety of metal complexes represented by metal complexes of 8-quinolinol derivatives, metal complexes of pyrromethene derivatives, rare earth metal complexes, and transition metal complexes, polymer compounds such as polythiophene, polyphenylene, and polyphenylenevinylene, and organic silane derivatives. Preferable examples include fused aromatic compounds, styryl compounds, diketopyrrolopyrrole compounds, oxazine compounds, pyrromethene metal complexes, transition metal complexes, lanthanoid complexes. More preferable examples include naphthacene, pyrene, chrysene, triphenylene, benzo[c]phenanthrene, benzo[a]anthracene, pentacene, perylene, fluoranthene, acenaphthofluoranthene, dibenzo[a,j]anthracene, diberizo[a,h]anthracene, benzo[a]naphthacene, hexacene, anthanthrene, naphtha[2,1-f]isoquinoline, α-naphthaphenanthridine, phenanthroxazole, quinolino[6,5-f]quinoline, and benzothiophanthrene. These compounds may be substituted with an aryl group, an aromatic heterocyclic group, a diarylamino group, or an alkyl group.

In the case where the aforementioned fluorescent light-emitting material is used as a fluorescent dopant and a host material is incorporated, the content of the fluorescent dopant in the light-emitting layer is in the range of 0.01 to 20 wt %, preferably in the range of 0.1 to 10 wt %.

When the light-emitting layer is a phosphorescent light-emitting layer, the layer contains a phosphorescent dopant and a host material. An organic metal complex containing at least one metal selected from ruthenium, rhodium, palladium, silver, rhenium, osmium, iridium, platinum, and gold is used as a phosphorescent dopant material. Such organic metal complexes are known in the aforementioned prior art technical documents and elsewhere and a suitable material may be selected from them and used.

Preferred phosphorescent dopants include complexes containing a noble metal element such as Ir in the center, typically Ir(ppy)3, complexes such as Ir(bt)2.acac3, and complexes such as PtOEt3. Specific examples of these complexes are illustrated below, but are not limited thereto.

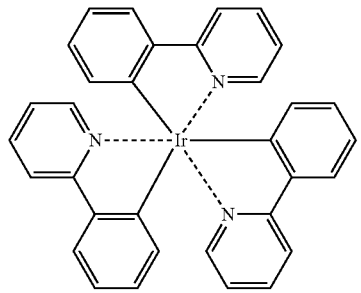

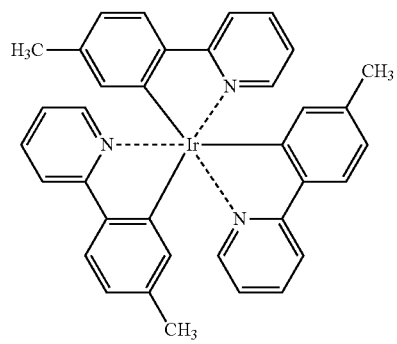

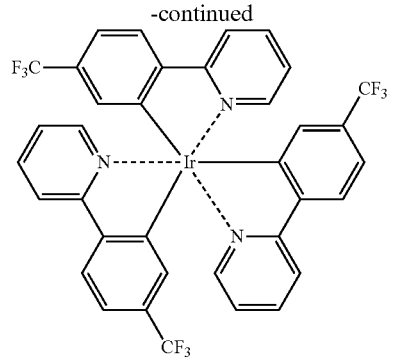
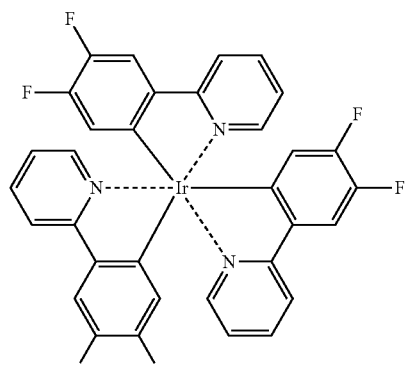
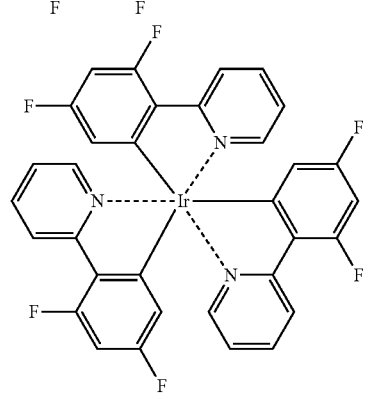
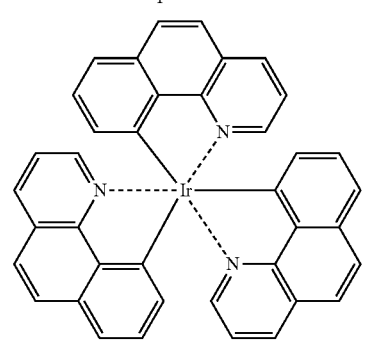
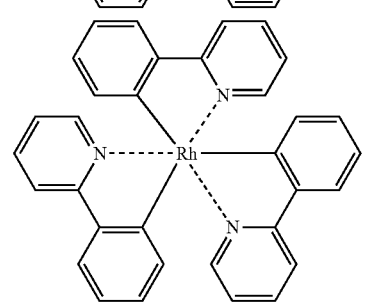
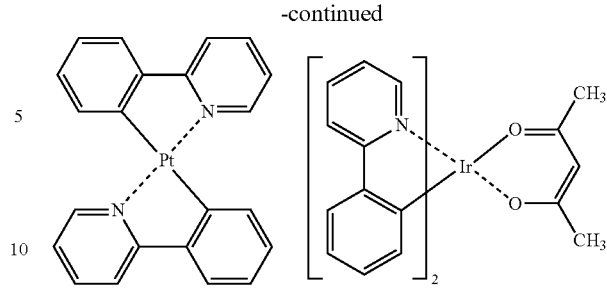
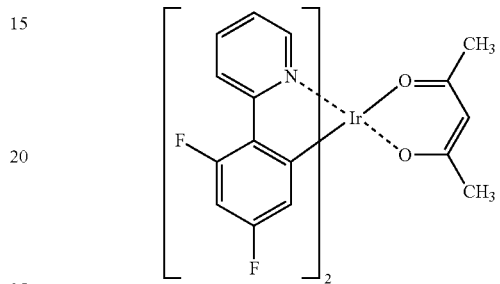
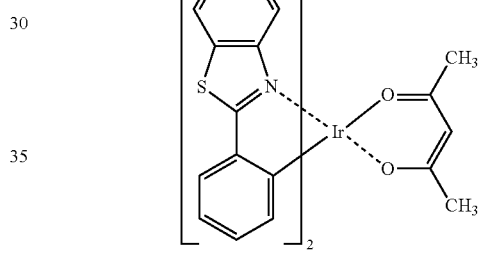
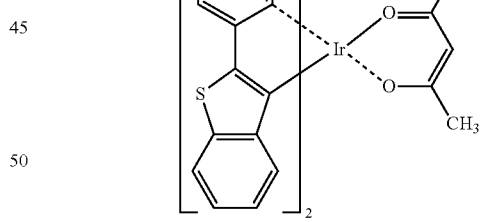
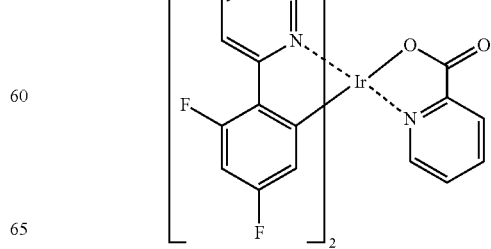

-continued

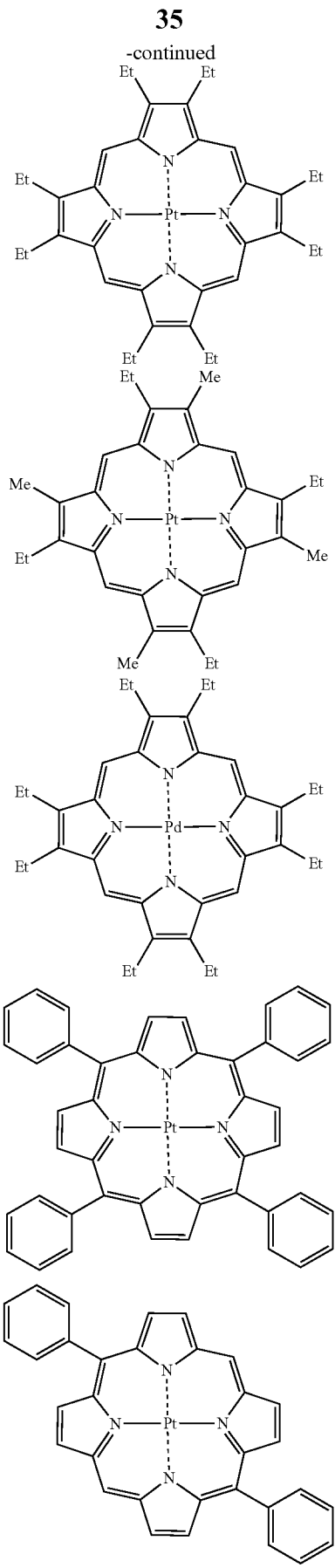

-continued

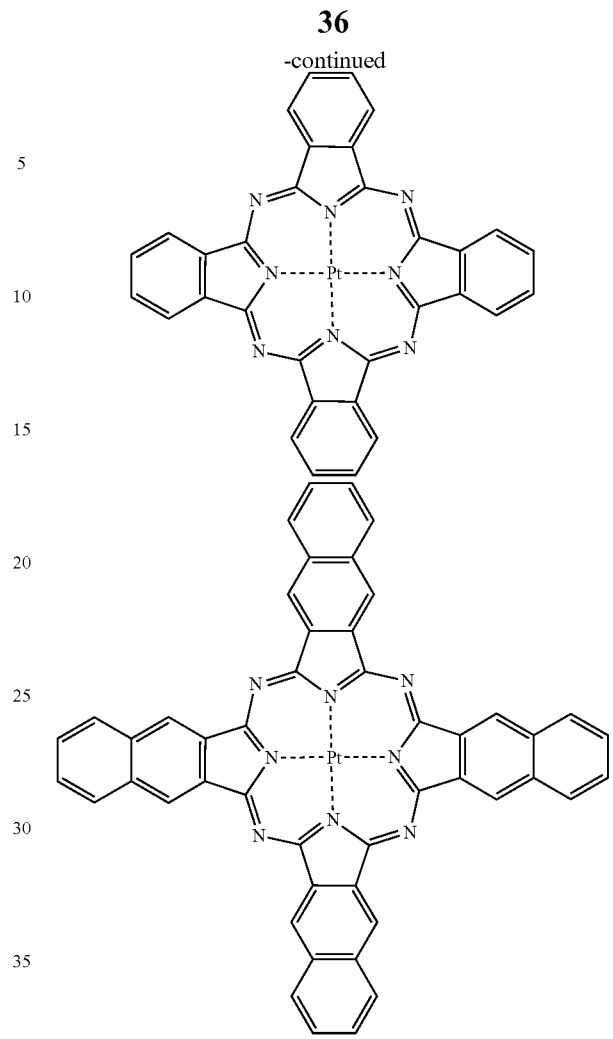

The content of the aforementioned phosphorescent dopant in the light-emitting layer is in the range of 1 to 50 wt %, preferably in the range of 5 to 30 wt %.

It is preferable to use a nitrogen-containing aromatic compound represented by the aforementioned general formula (1) as a host, material in the light-emitting layer. However, in the case where the said compound is used in any of the organic layers other than the light-emitting layer, a host material other than a compound represented by general formula (1) may be used in the light-emitting layer. Further, a compound represented by general formula (1) may be used together with other host material. Still further, plural kinds of known host materials may be used together.

Among the known host compounds, those suitable for use preferably have a hole transport ability or an electron transport ability, can prevent the wavelength of emitted light from shifting to longer wavelengths, and have a high glass transition temperature.

Such host materials are known in a large number of patent documents and elsewhere and a suitable material may be selected from them. Specific examples include, but are not limited to, indole derivatives, carbazole derivatives, triazole derivatives, oxazole derivatives, oxadiazole derivatives, imidazole derivatives, polyarylalkane derivatives, pyrazoline derivatives, pyrazolone derivatives, phenylenediamine derivatives, arylamine derivatives, amino-substituted chalcone derivatives, styrylanthracene derivatives, fluorenone derivatives, hydrazone derivatives, stilbene derivatives, silazane derivatives, aromatic tertiary amine compounds, styrylamine compounds, aromatic dimethylidene-based compounds, porphyrin-based compounds, anthraquinodimethan derivatives, anthrone derivatives, diphenylquinone derivatives, thiopyran dioxide derivatives, heterocyclic tetracarboxylic acid anhydrides of naphthalene and perylene, a variety of metal complexes represented by metal complexes of phthalocyanine derivatives and 8-quinolinol derivatives, metal phthalocyanines, and metal complexes of benzoxazole derivatives and benzothiazole derivatives, and polymer compounds such as polysilane-based compounds, poly(N-vinylcarbazole) derivatives, aniline-based copolymers, thiophene oligomers, polythiophene derivatives, polyphenylene derivatives, polyphenylenevinylene derivatives, and polyfluorene derivatives.

—Injecting Layer—

The injecting layer is a layer that is provided between an electrode and an organic layer to reduce the driving voltage and improve the luminance. The injecting layer includes a hole-injecting layer and an electron-injecting layer and may be provided respectively between the anode and the light-emitting layer or the hole-transporting layer and between the cathode and the light-emitting layer or the electron-transporting layer. The injecting layer may be provided according to the need.

—Hole-Blocking Layer—

The hole-blocking layer has a function of the electron-transporting layer in a broad sense and is composed of a hole-blocking material that has an extremely poor ability to transport holes while having a function of transporting electrons. The hole-blocking layer can improve the probability of recombination of electrons and holes by transporting electrons while blocking holes.

A compound represented by general formula (1) may be used in the hole-blocking layer. However, in the case where the said compound is used in any of the organic layers other than the hole-blocking layer, a known hole-blocking material may be used instead. Further, any of the materials for the electron-transporting layer to be described later on may be used as a hole-blocking material according to the need.

—Electron-Blocking Layer—

The electron-blocking layer is made from a material that has an extremely poor ability to transport electrons while having a function of transporting holes and it can improve the probability of recombination of electrons and holes by transporting holes while blocking electrons.

As a material for the electron-blocking layer, a compound represented by the aforementioned general formula (1) is preferably used. However, in the case where the said compound is used in any of the organic layers other than the electron-blocking layer, any of the materials for the hole-transporting layer to be described later on may be used instead according to the need. The thickness of the electron-blocking layer is preferably 3 to 100 nm, more preferably 5 to 30 nm.

—Exciton-Blocking Layer—

The exciton-blocking layer is a layer for preventing excitons that are generated by recombination of holes and electrons in the light-emitting layer from diffusing to the charge-transporting layer. The insertion of this layer makes it possible to efficiently confine excitons in the light-emitting layer and enhance the luminous efficiency of the device. The exciton-blocking layer may be inserted either on the anode side or on the cathode side adjacent to the light-emitting layer or simultaneously on both the anode and the cathode sides.

A compound represented by the aforementioned general formula (1) may be used as a material for the exciton-blocking layer. However, in the case where the said compound is used in any of the organic layers other than the exciton-blocking layer, a compound such as 1,3-dicarbazolylbenzene (mCP) and bis(2-methyl-8-quinolinolato)-4-phenylheolatoaluminum(III) (BAlq) may be used instead.

—Hole-Transporting Layer—

The hole-transporting layer is made from a hole-transporting material that has a function of transporting holes and it may be provided in a single layer or a plurality of layers.

The hole-transporting material has either a property of injecting or transporting holes or a property of constituting a barrier to electrons and it may be an organic substance or an inorganic substance. It is preferable to use a compound represented by the aforementioned general formula (1) in the hole-transporting layer. However, in the case where the said compound is used in any of the organic layers other than the hole-transporting layer, a suitable material may be selected from the known compounds and used. Specific examples of known hole-transporting materials suitable for use include triazole derivatives, oxadiazole derivatives, imidazole derivatives, polyarylalkane derivatives, pyrazoline derivatives, pyrazolone derivatives, phenylenediamine derivatives, aromatic amine derivatives, amino-substituted chalcone derivatives, oxazole derivatives, styrylanthracene derivatives, fluorenone derivatives, hydrazone derivatives, stilbene derivatives, silazane derivatives, aniline-based copolymers, porphyrin compounds, styrylamine compounds, and electrically conductive oligomers, particularly thiophene oligomers. Preferable examples include porphyrin compounds, aromatic tertiary amine compounds, and styrylamine compounds and more preferable examples include aromatic tertiary amine compounds.

—Electron-Transporting Layer—

The electron-transporting layer is made from a material that has a function of transporting electrons and may be provided in a single layer or a plurality of layers.

An electron-transporting material (serving also as a hole-blocking material in sonic cases) is acceptable as such so long as it has a function of transporting electrons that are injected from the cathode to the light-emitting layer. A compound represented by general formula (1) may be used in the electron-transporting layer. However, in the case where the said compound is used in any of the organic layers other than the electron-transporting layer, a suitable material may be selected from the known compounds and used. Examples of such known compounds include nitro-substituted fluorene derivatives, diphenylquinone derivatives, thiopyran dioxide derivatives, carbodiimide, fluorenylidenemethane derivatives, anthraquinodimethan derivatives, anthrone derivatives, and oxadiazole derivatives. Further, thiadiazole derivatives that are derived from the aforementioned oxadiazole derivatives by substituting a sulfur atom for the oxygen atom of the oxadiazole ring and quinoxaline derivatives that have a quinoxaline ring known as an electron-withdrawing group may be used as electron-transporting materials. Further, polymer materials that contain any of these materials in the polymer chain or polymer materials whose backbone is constituted of any of these materials may be used.

EXAMPLES

This invention is explained in more detail hereinafter with reference to the examples. However this invention is not limited to the examples and can be reduced to practice in various modes unless such a practice exceeds the gist of this invention.

The compounds represented by general formula (1) that are used in this invention were synthesized by the routes shown below. The compound numbers correspond to the numbers assigned to the aforementioned chemical formulas.

Synthetic Example 1

Synthesis of Compound 1-9

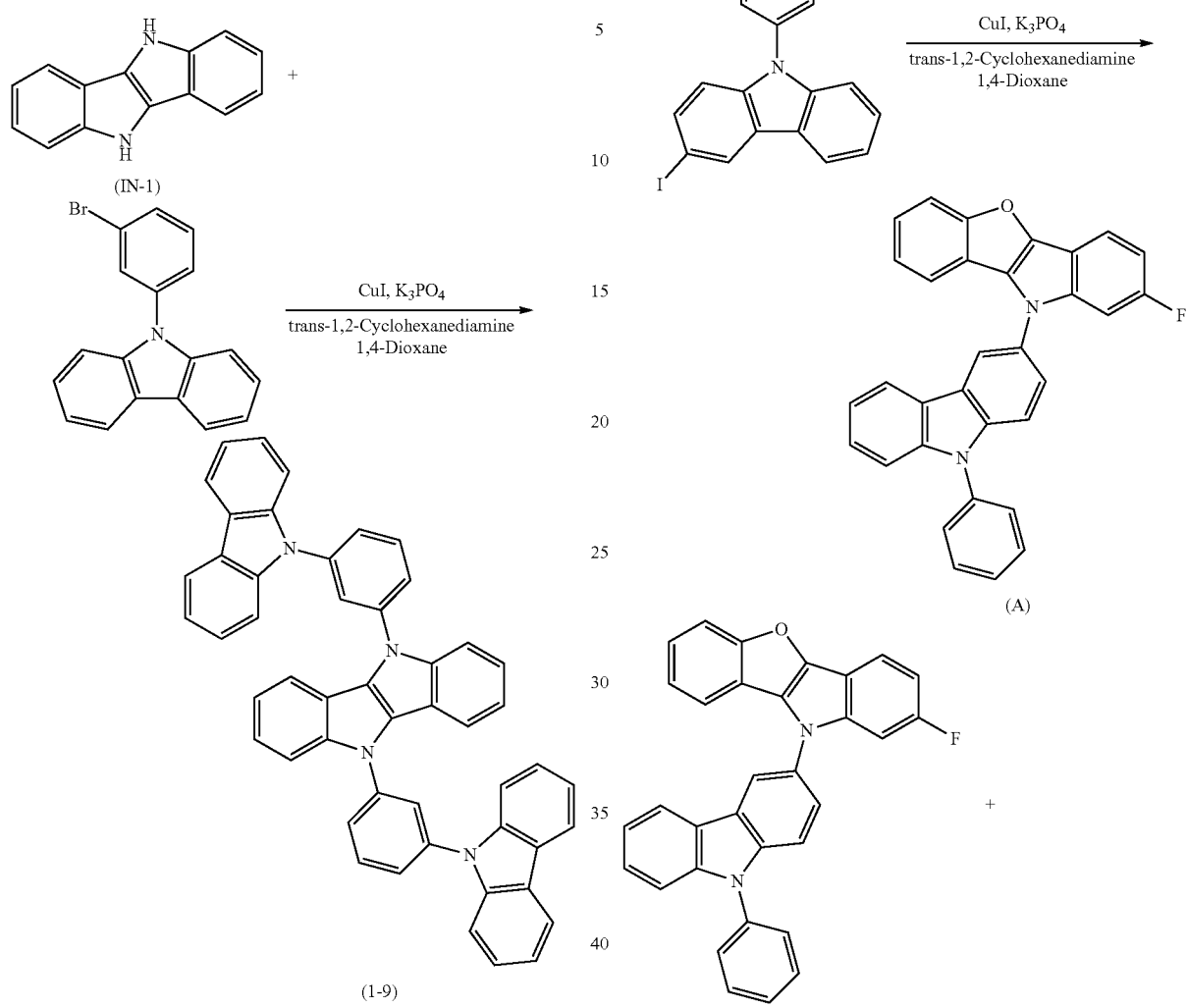

Under a nitrogen atmosphere, 2.8 g (8.8 mmol) of 3-bromophenyl-9-carbazole, 0.9 g (3.8 mmol) of indolo[3,2-b]indole (IN-1), 0.34 g (1.8 mmol) of copper iodide, 11.3 g (53.3 mmol) of tripotassium phosphate, 2.0 g (17.5 mmol) of trans-1,2-cyclohexanediamine, and 100 mL of 1,4-dioxane were heated at 120° C. for 18 hours with stirring. The reaction solution was cooled to room temperature, then the precipitated crystal was collected by filtration and the solvent was distilled off under reduced pressure. The residue this obtained was purified by silica gel column chromatography to give 1.7 g (2.6 mmol, 69 mol % yield) of Compound 1-9. The results of ED-MS indicate that m/z=689 [M+H]$^+$ and this confirms that the product is the target compound.

Synthetic Example 2

Synthesis of Compound 2-13

Under a nitrogen atmosphere, 3.4 g (15 mmol) of 9-fluorobenzofuro[3,2-b]indole, 5.5 g (15 mmol) of 3-iodo-9-phenylcarbazole, 0.34 g (1.8 mmol) of copper iodide, 11.3 g (53.3 mmol) of tripotassium phosphate, 2.0 (17.5 mmol) of trans-1,2-cyclohexanediamine, and 100 mL of 1,4-dioxane were heated at 120° C. for 18 hours with stirring. The reaction solution was cooled to room temperature, then the precipitated crystal was collected by filtration and the solvent was distilled off under reduced pressure. The residue thus obtained was purified by silica gel column chromatography to give 5.3 g (11 mmol, 76 mol % yield) of Intermediate A.

Under a nitrogen atmosphere, 0.41 g (9.6 mmol) of sodium hydride (62.9% dispersion) and 20 mL of dehydrated DMF were stirred at room temperature for 30 minutes. To the suspension thus obtained was added a solution of 1.5 g (8.8 mmol) of carbazole in DMF (20 mL) and the mixture was stirred at room temperature for 30 minutes. To the suspension was added 4.1 g (8.8 mmol) of Intermediate A and the mixture was stirred at 60° C. for 30 minutes. The reaction mixture was cooled to room temperature, distilled water (100 mL) was added to the mixture with stirring, and the precipitated light yellow solid was collected by filtration. The light yellow solid thus obtained, was purified by silica gel column chromatography and hot reslurrying to give 3.2 g (5.3 mmol, 60 mol % yield) of Compound 2-13 as a white solid. The results of FD-MS indicate that m/z=614 [M+H]$^+$ and this confirms that the product is the target compound.

Synthetic Example 3

Synthesis of Compound 3-11

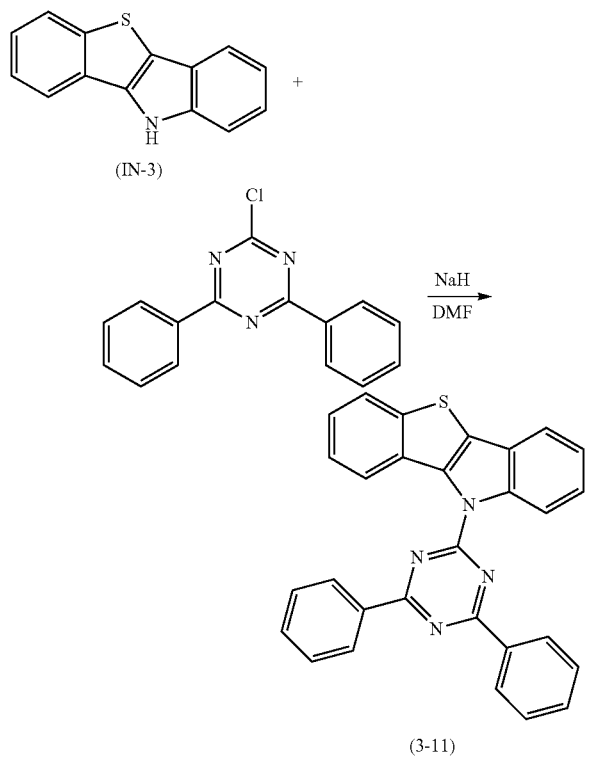

Under a nitrogen atmosphere, 0.34 g (8.8 mmol) of sodium hydride (62.2% dispersion) and 20 mL of dehydrated DMF were stirred at room temperature for 30 minutes. To the suspension thus obtained was added a solution of 2.0 g (8.8 mmol) of benzothieno[3,2-b]indole (IN-3) in DMF (20 mL) and the mixture was stirred at room temperature for 30 minutes. To the suspension was added 2.4 g (8.8 mmol) of diphenylchlorotriazine and the mixture was stirred at 60° C. for 2 hours. The reaction mixture was cooled to room temperature, distilled water (100 mL) was added to the mixture with stirring, and the precipitated light yellow solid was collected by filtration. The light yellow solid thus obtained was purified by silica gel column chromatograph to give 7.3 g (7.2 mmol, 82 mol % yield) of Compound 3-11. The results of FD-MS indicate that m/z=455 [M+H]$^+$ and this confirms that the product is the target compound.

Compound 1-2, Compound 1-13, Compound 1-19, Compound 2-1, Compound 2-17, Compound 3-15, and Compound 3-17 were synthesized according to the methods described in the aforementioned Synthetic Examples and in the specification and used in the fabrication of organic EL devices.

Example 1

The constituent layers were deposited in thin film by the vacuum deposition process at a degree of vacuum of $4.0 \times 10^{-5}$ Pa one upon another on a glass substrate on which a 110 nm-thick indium tin oxide (ITO) anode had been formed. First, copper phthalocyanine (CuPc) was deposited on the ITO anode to a thickness of 25 nm. Then, 4,4'-bis[N-(1-naphthyl)-N-phenylamino]biphenyl (NPB) was deposited to a thickness of 55 am as a hole-transporting layer. Next. Compound 1-9 obtained in Synthetic Example 1 as a host material and bis(2-(2'-benzo[4,5-a]thienyl)pyridinato-N,C3)iridium (acetylacetonate) [(Btp)2Iraca] as a phosphorescent dopant were co-deposited from different deposition sources to a thickness of 47.5 nm to form a light-emitting layer. The concentration of (Btp)2Iracac in the light-emitting layer was 8.0 wt %. Next, tris(8-hydroxyquinolinato)aluminum(III) (Alq3) was deposited to a thickness of 30 nm as an electron-transporting layer. Further, lithium fluoride (LiF) was deposited on the electron-transporting layer to a thickness of 1.0 nm as an electron-injecting layer. Finally, aluminum (Al) was deposited as an electrode on the electron-injecting layer to a thickness of 200 nm to complete the fabrication of an organic EL device.

The organic EL device thus fabricated was connected to an external power source and, when direct current voltage was applied, the device was confirmed to have the luminous characteristics shown in Table 1. In Table 1, the values of the luminance, voltage, and luminous efficiency are values obtained when the device was driven at 10 mA/cm$^2$. The peak wavelength of the spectrum of light emitted from the device is 620 nm and this proves that light is emitted from (Btp)2Iracac.

Example 2

An organic EL device was fabricated as in Example 1 except that Compound 2-13 was used as the host material in the light-emitting layer.

Example 3

An organic EL device was fabricated as in Example 1 except that Compound 3-11 was used as the host material in the light-emitting layer.

Example 4

An organic EL device was fabricated as in Example 1 except that Compound 1-2 was used as the host material in the light-emitting layer,

Example 5

An organic EL device was fabricated as in Example 1 except that Compound 1-13 was used as the host material in the light-emitting layer.

Example 6

An organic EL device was fabricated as in Example 1 except that Compound 1-19 was used as the host material in the light-emitting layer.

Example 7

An organic EL device was fabricated as in Example 1 except that Compound 2-1 was used as the host material in the light-emitting layer.

Example 8

An organic EL device was fabricated as in Example 1 except that Compound 2-17 was used as the host material in the light-emitting layer.

Example 9

An organic EL device was fabricated as in Example 1 except that Compound 3-15 was used as the host material in the light-emitting layer.

Example 10

An organic EL device was fabricated as in Example 1 except that Compound 3-17 was used as the host material in the light-emitting layer.

Comparative Example 1

An organic EL device was fabricated as in Example 1 except that bis(2-methyl-8-quinolinolato)-4-phenylphenolatoaluminum(III) (BAN) was used as the host material in the light-emitting layer.

Comparative Example 2

An organic EL device was fabricated as in Example 1 except that Compound H-1 shown below was used as the host material in the light-emitting layer. The peak wavelength of the spectrum of light emitted from the device is 620 nm and this proves that light is emitted from (Btp)2Iracac. The luminous characteristics are shown in Table 1.

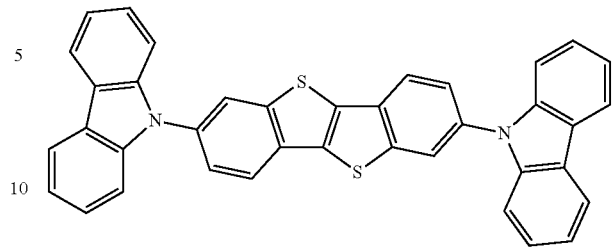

H-1

The peak wavelength of the spectrum of light emitted from each of the devices fabricated in Examples 1 to 10 and Comparative Examples 1 and 2 is $20 nm and this proves that light is emitted from (Btp)2Iracac. The are shown in Table 1.

TABLE 1

| | host material | luminous characteristics (@10 mA/cm$^2$) | | |
|---|---|---|---|---|
| | | values of the luminance (cd/m$^2$) | voltage (V) | luminous efficiency (1 m/W) |
| Example 1 | 1-9 | 1223 | 5.7 | 6.2 |
| Example 2 | 2-13 | 1240 | 5.9 | 5.9 |
| Example 3 | 3-11 | 1302 | 5.0 | 6.7 |
| Example 4 | 1-2 | 1032 | 7.8 | 4.9 |
| Example 5 | 1-13 | 1121 | 6.2 | 4.1 |
| Example 6 | 1-19 | 1279 | 5.9 | 6.1 |
| Example 7 | 2-1 | 1159 | 7.2 | 3.8 |
| Example 8 | 2-17 | 1197 | 6.0 | 5.8 |
| Example 9 | 3-15 | 1202 | 7.1 | 3.9 |
| Example 10 | 3-17 | 1108 | 6.0 | 5.7 |
| Comparative example 1 | BAlq | 1020 | 8.4 | 3.8 |
| 2 | H-1 | 1092 | 8.1 | 3.8 |

It is apparent from Table 1 that a nitrogen-containing aromatic compound represented by general formula (1) to be used in an organic EL device according to this invention exhibits better luminous characteristics than BAlq, a compound generally known as a phosphorescent host. Further, the compound exhibits better luminous characteristics than Compound H-1 that does not have a nitrogen atom in the central skeleton and this indicates the superiority of the aforementioned nitrogen-containing aromatic compound.

Industrial Applicability

A nitrogen-containing aromatic compound to be used in an organic electroluminescent device according to this invention has a skeleton resulting from [3,2-b]-fusion of indole to a fused heterocycle consisting of a five-membered ring and a six-membered ring. This skeleton can be converted to a skeleton that is capable of maintaining a hole transport property or an electron transport property depending upon the kind of substituent to be introduced. This probably explains why the compounds to be used in this invention exhibit good injection and transport characteristics of holes and electrons. This nitrogen-containing aromatic compound seems to exhibit excellent luminous characteristics particularly when it is used in the light-emitting layer because the compound is characterized by having properties of causing electric charges to be well balanced thereby improving the probability of their recombination and, further, of having high energy in the lowest triplet excited state thereby effectively suppressing transfer of the triplet excitation energy from the dopant to the host molecule. In addition, the compound exhibits good properties in the amorphous state and is highly heat-resistant and electrochemically stable. It is likely that these properties help realize organic EL devices of long driving life and good durability.

The organic EL device of this invention satisfies a level of performance required for practical use with respect to the luminous characteristics, driving life, and durability and is of high technical value because of its potential applicability to flat panel displays (cellular phone display devices, vehicle-mounted display devices, office computer display devices, and television sets), light sources utilizing the characteristics of planar light emitters (illumination, light sources for copying machines, and backlight sources for liquid crystal displays and meters), display boards, and marker lamps.

The invention claimed is:

1. An organic electroluminescent device comprising an anode, a plurality of organic layers, and a cathode piled one upon another on a substrate wherein at least one of the organic layers contains a compound represented by the following general formula (1);

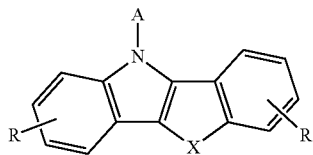

(1)

In general formula (1), X is N-A, an oxygen atom, or a sulfur atom; each A is independently an alkyl group of 1 to 10 carbon atoms, a cycloalkyl group of 3 to 11 carbon atoms, an aromatic hydrocarbon group of 6 to 30 carbon atoms, or an aromatic heterocyclic group of 3 to 30 carbon atoms exclusive of a fused heterocycle consisting of 4 rings or more; each R is independently a hydrogen atom, an alkyl group of 1 to 10 carbon atoms, a cycloalkyl group of 3 to 11 carbon atoms, an aromatic hydrocarbon group of 6 to 18 carbon atoms, or an aromatic heterocyclic group of 3 to 18 carbon atoms exclusive of a fused heterocycle consisting, of 4 rings or more.

2. An organic electroluminescent device as described in claim 1 wherein, in general formula (1), each A is independently an aromatic hydrocarbon group of 6 to 30 carbon atoms or an aromatic heterocyclic group of 3 to 30 carbon atoms exclusive of a fused heterocycle consisting of 4 rings or more.

3. An organic electroluminescent device as described in claim 2 wherein the layer containing a compound represented by general formula (1) is at least one layer selected, from the group consisting of a light-emitting layer, a hole-transporting layer, and an electron-blocking layer.

4. An organic electroluminescent device as described in claim 3 wherein the layer containing a compound represented by general formula (1) is a light-emitting layer containing a phosphorescent dopant.

5. An organic electroluminescent device as described in claim 1 wherein, in general formula (1), X is N-A.

6. An organic electroluminescent device as described in claim 5 wherein the layer containing a compound represented by general formula (1) is at least one layer selected from the group consisting of a light-emitting layer, a hole-transporting layer, and an electron-blocking layer.

7. An organic electroluminescent device as described in claim 6 wherein the layer containing a compound represented by general formula (1) is a light-emitting layer containing a phosphorescent dopant.

8. An organic electroluminescent device as described in claim 1 wherein, in general formula (1), X is an oxygen atom or a sulfur atom.

9. An organic electroluminescent device as described in claim 8 wherein the layer containing a compound represented by general formula (1) is at least one layer selected from the group consisting of a light-emitting layer, a hole-transporting layer, and an electron-blocking layer.

10. An organic electroluminescent device as described in claim 9 wherein the layer containing a compound represented by general formula (1) is a light-emitting layer containing a phosphorescent dopant.

11. An organic electroluminescent device as described in claim 1 wherein the layer containing a compound represented by general formula (1) is at least one layer selected from the group consisting of a light-emitting layer, a hole-transporting layer, and an electron-blocking layer.

12. An organic electroluminescent device as described in claim 11 wherein the layer containing a compound represented by general formula (1) is a light-emitting layer containing a phosphorescent dopant.

* * * * *